US 11,738,869 B2

(12) United States Patent
Bouyer et al.

(10) Patent No.: US 11,738,869 B2
(45) Date of Patent: Aug. 29, 2023

(54) DEVICE AND METHOD FOR DROPPING FRAGILE PRODUCTS

(71) Applicant: Centre de Cooperation Internationale en Recherche Agronomique Pour le Developpement, Paris (FR)

(72) Inventors: Jérémy Bouyer, Soubès (FR); Momar Talla Seck, Dakar (SN); Geoffrey Gimonneau, Bobo-Dioulasso (BF)

(73) Assignee: Centre de Cooperation Internationale en Recherche Agronomique Pour Le Developpement, Paris (FR)

( * ) Notice: Subject to any disclaimer, the term of this patent is extended or adjusted under 35 U.S.C. 154(b) by 1303 days.

(21) Appl. No.: 16/098,242

(22) PCT Filed: Apr. 25, 2017

(86) PCT No.: PCT/EP2017/059832
§ 371 (c)(1),
(2) Date: Nov. 1, 2018

(87) PCT Pub. No.: WO2017/190991
PCT Pub. Date: Nov. 9, 2017

(65) Prior Publication Data
US 2019/0141946 A1    May 16, 2019

(30) Foreign Application Priority Data

May 3, 2016    (FR) ...................................... 1653994

(51) Int. Cl.
*A01K 67/033*    (2006.01)
*B64D 1/16*    (2006.01)
(Continued)

(52) U.S. Cl.
CPC .............. *B64D 1/16* (2013.01); *A01K 67/033* (2013.01); *A01K 67/0333* (2013.01); *A61D 1/00* (2013.01); *B64U 2101/00* (2023.01)

(58) Field of Classification Search
CPC .... A01K 67/033; A01K 67/0333; B64D 1/16; A61D 1/00; B64U 2101/00
See application file for complete search history.

(56) References Cited

U.S. PATENT DOCUMENTS 3,118,575 A    1/1964    McCauley
4,260,108 A    4/1981    Maedgen, Jr.
(Continued)

FOREIGN PATENT DOCUMENTS

CN    105197244 A    12/2015

OTHER PUBLICATIONS

International Search Report issued in corresponding International Patent Application No. PCT/EP2017/059832 dated Jun. 26, 2017.

*Primary Examiner* — Monica L Perry
*Assistant Examiner* — Aaron M Rodziwicz
(74) *Attorney, Agent, or Firm* — Morgan, Lewis & Bockius LLP

(57) ABSTRACT

A device (10) for dropping fragile products (5) comprising:—a storage means (4) for storing said products, comprising a discharge means (4a) for discharging said products, —a means for distributing the fragile products comprising at least one cavity (1a, 1b) provided in the surface of a support (2), the support being capable of assuming at least two positions, a first position in which the at least one cavity is located opposite and at a distance from said discharge means and can be filled with fragile products, and a second position in which said cavity is spaced apart from said discharge means and can be emptied, said device further comprising a flexible means (3) for bringing the discharge means with the (Continued)

Figure 1:
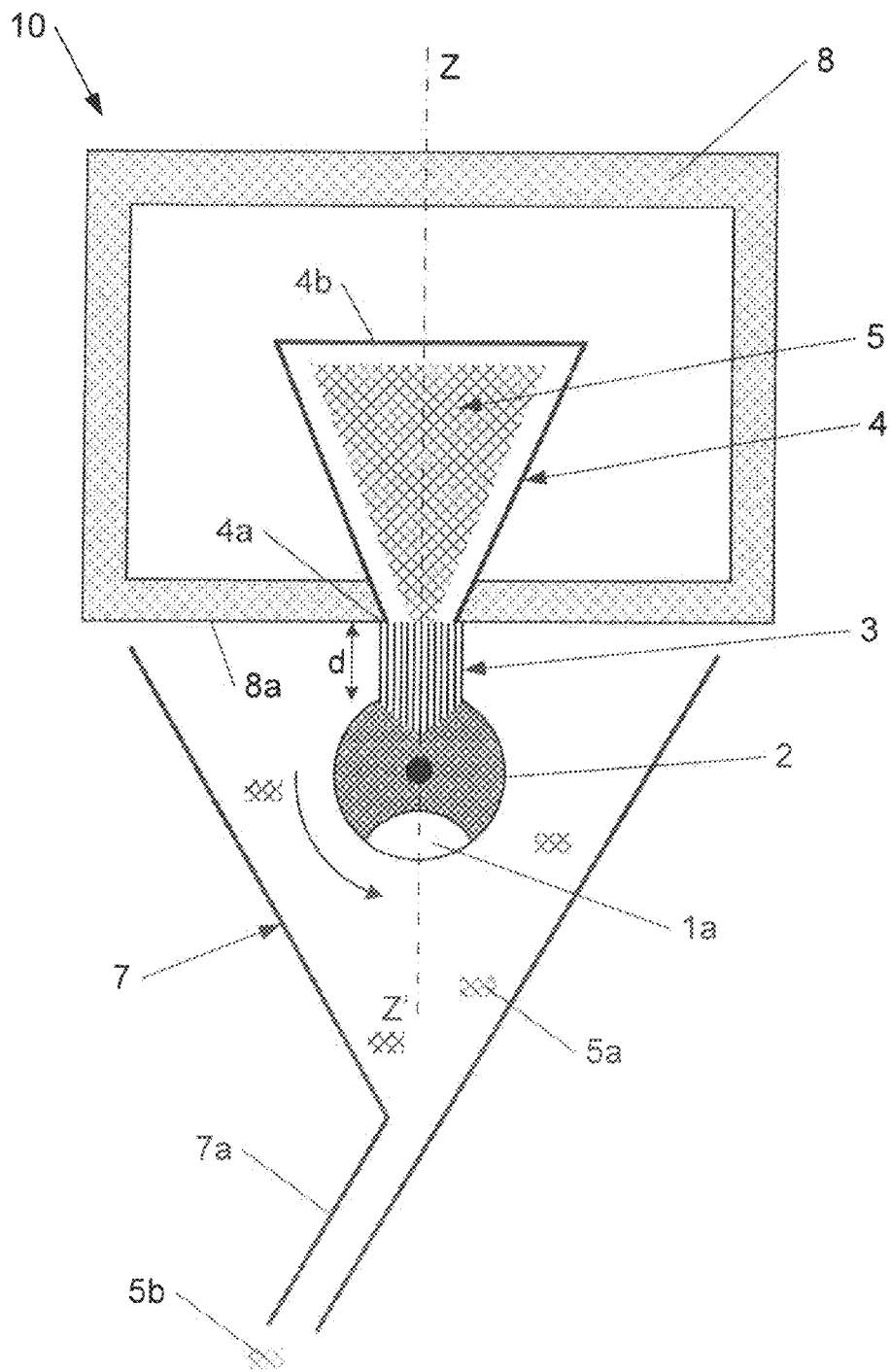

at least one cavity into communication in order to fill said cavity with fragile products.

16 Claims, 3 Drawing Sheets

(51) Int. Cl.
  *A61D 1/00* (2006.01)
  *B64U 101/00* (2023.01)

(56) References Cited

U.S. PATENT DOCUMENTS

| | | | |
|---|---|---|---|
| 4,537,333 A | 8/1985 | Bjerregaard | |
| 5,074,247 A * | 12/1991 | Gupta | A01K 1/031 |
| | | | 119/6.5 |
| 5,148,989 A | 9/1992 | Skinner | |
| 5,178,094 A * | 1/1993 | Carr | A01K 67/033 |
| | | | 119/6.5 |
| 5,794,847 A | 8/1998 | Stocker | |
| 6,244,213 B1 * | 6/2001 | Tedders | A01K 67/033 |
| | | | 119/6.6 |
| 6,532,891 B2 * | 3/2003 | Gaugler | A01K 67/033 |
| | | | 119/6.7 |
| 10,188,084 B2 * | 1/2019 | Leo | A23K 20/163 |
| 10,212,949 B2 * | 2/2019 | Leo | A21D 6/00 |
| 10,264,769 B2 * | 4/2019 | Leo | A23K 20/163 |
| 2012/0060446 A1 * | 3/2012 | Merz | B65B 37/20 |
| | | | 53/167 |
| 2013/0319334 A1 * | 12/2013 | Newton | A01K 67/033 |
| | | | 119/51.01 |
| 2014/0020630 A1 * | 1/2014 | Courtright | A01K 67/033 |
| | | | 119/6.6 |
| 2015/0041596 A1 | 2/2015 | Markov | |
| 2015/0122182 A1 * | 5/2015 | Aldana | A01K 67/033 |
| | | | 119/6.6 |
| 2015/0296760 A1 * | 10/2015 | Perednia | A01K 67/033 |
| | | | 119/6.5 |
| 2016/0066552 A1 * | 3/2016 | Arsiwalla | A01K 1/0047 |
| | | | 119/6.5 |
| 2017/0359943 A1 * | 12/2017 | Calleija | A62C 37/40 |

* cited by examiner

DEVICE AND METHOD FOR DROPPING FRAGILE PRODUCTS

The invention concerns a device for dropping in the atmosphere fragile products such as insects without damaging them and in controlled quantities. The invention also relates to a method for dropping, which implements the device and a transport means equipped with such a device.

The dropping of insects sterilised by irradiation or genetically modified in a natural environment has become a major way to fight certain diseases: malaria and arboviruses (Chikungunya, Dengue, Zika) with mosquitoes, African trypanosomiasis (sleeping sickness in humans and Nagana in animals) with the tsetse fly.

The dropped insects have been sterilised by irradiation or genetically modified so that their offspring is not viable. They come into competition with natural insects and contribute to their eradication. This enables to avoid the large-scale diffusion of pesticides. In other applications, parasitoids are dropped, for example Trichogrammae. These parasitoids feed off the larvae of harmful insects.

The drop must be performed in precisely-determined quantities as the device is intended for dropping products that are expected to have an effect on the environment, and the drop must enable to achieve a measurable effect in a predefined area.

Several devices for dropping fragile products in a natural environment and in precisely-measured quantities are known. One of the ways consists of using a worm drive. This system presents the disadvantage of damaging a large proportion of the fragile products. Devices using a vibration table are also known. The operation of these devices is disrupted by the vibration of the transport means (light aircraft) in which they are loaded on, and therefore lose the accuracy thereof. Finally, devices using a belt conveyor are also known, but they cannot be used to drop small quantities of insects and they injure the insects (see for example MXNL05000060).

For this purpose, the invention proposes a device for the dropping of fragile products comprising:
  a storage means of said products, comprising a discharge means of said products,
  a distribution means of the fragile products comprising at least one cavity provided at the surface of a support, the support being capable of taking at least two positions, a first position wherein the at least one cavity is located facing and at a distance of said discharge means and can be filled with fragile products, and a second position wherein said cavity is spaced apart from said discharge means and can be emptied,
  said device further comprising a flexible means of bringing the discharge means into communication with at least one cavity in order to fill said cavity with fragile products.

The device comprises mainly a means to store the fragile products to be dropped, such as a hopper, and a means to distribute the fragile products. The hopper conventionally comprises a discharge means, such as a narrowing and an orifice in the lower section during operations.

The distribution means comprises a support with cavities on the surface, i.e. open cavities that can be filled and then emptied. The support can be animated with a motion, such as rotation or back-and-forth, as will be described below, enabling, in the first position, to present a cavity facing the orifice of the discharge means of the hopper and, in the second position, to move this cavity away from the hopper.

In the first position, the cavity is filled, by gravity, with fragile products, and in the second position it is emptied.

This arrangement, in itself, enables to control the dropping of fragile products, since the volume of the cavities and the frequency at which they present themselves in front of the orifice of the hopper can be adjusted by the user.

The difficulty consists of, on the one hand, avoiding the dispersion of the fragile products in the first position of the support, when the products pass from the hopper into the cavity, and on the other hand, avoiding damages to the fragile products when passing from the first to the second position of the support.

For this purpose:
  on the one hand, the support is located at a distance from the discharge means: this enables to avoid the fragile products from being damaged by shear effect between the discharge means and the sides of the cavity.
  on the other hand, the device comprises a flexible communication means for the fragile products that extend between the discharge means and the support; this communication means channels the fragile products from the orifice of the hopper towards a cavity located facing said orifice.

According to the characteristics of the invention, which can be taken individually or in combination:
  the communication means can extend from the periphery of the discharge means,
  the communication means can define a volume connecting the discharge means and the support,
  the communication means can comprise flexible components provided to ensure the guiding of the products when they fall in a cavity located facing the discharge means; in another embodiment, the communication means is simply a flexible tube,
  the free end of the flexible components is in contact with the surface of the support, particularly with the periphery of a cavity when this cavity is facing the discharge means; the communication means are therefore provided to sweep the surface of the support as the latter is in motion, thereby reducing the shear effect on the fragile products,
  the flexible components are threads, filaments, hairs or thin strips,
  the support can be a sphere rotationally mounted or a cylinder rotationally mounted about an axis,
  the at least one cavity can be of a hemispherical shape,
  the device can comprise an ejection means capable of collecting the products that have exited a cavity and to guide them towards the exterior of the device,
  the device can comprise an enclosure that forms a thermal barrier, said enclosure enclosing the storage means,
  the device can further comprise a control means provided particularly to adjust the speed of motion of the support.

The invention also relates to a vehicle, such as an aircraft, comprising a device according to the invention.

The invention also relates to a method for dropping insects using a device according to the invention, comprising steps consisting of:
  Filling the storage means with insects,
  Activating the support so as to drop the insects.

The method can further comprise a prior step consisting of cooling the storage means, so as to make or keep the insects lethargic.

It can also comprise a prior step consisting of loading the device into a vehicle such as an aircraft so as to drop the insects in flight.

Advantageously, the insects are sterilised by irradiation or genetically modified so that the offspring thereof is not viable.

Figure 2:
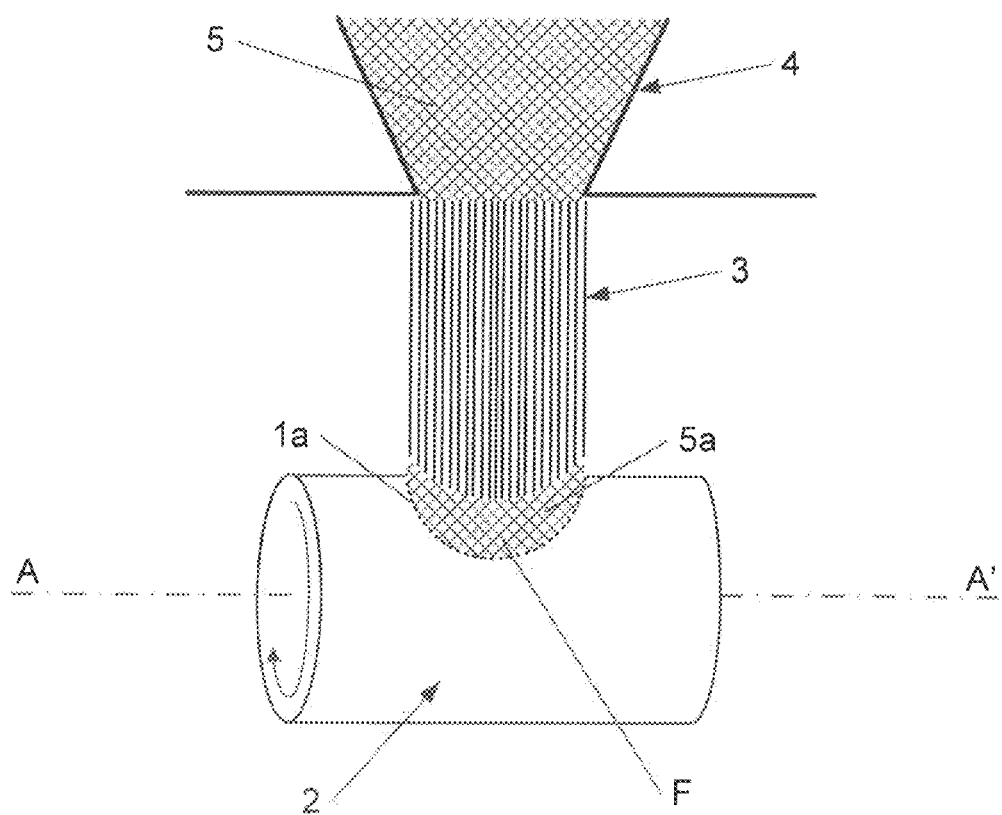
Figure 3A:
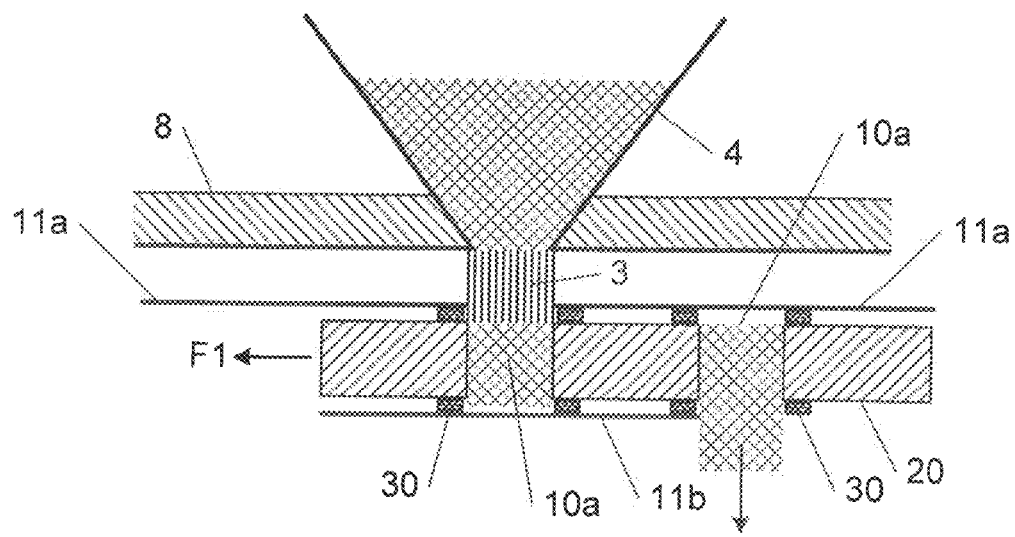
Figure 3B:
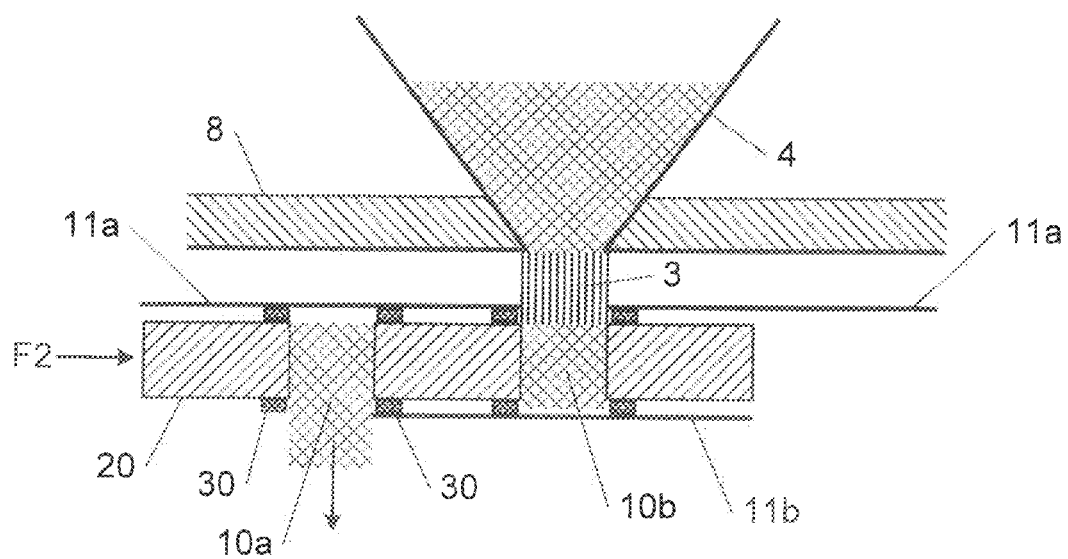

Embodiments and different variants are described below, as non-limiting examples, with reference to the appended drawings, wherein:

FIG. 1 schematically represents a device in elevation,

FIG. 2 represents a magnified view of the catch area of the products,

FIGS. 3A and 3B schematically represent a cross-sectional view of another embodiment of the invention.

FIGS. 1 and 2 represent a device 10 for dropping fragile products 5, for example insects. The device 10 is represented in the operating position thereof, the notions of top and bottom, lower and upper, will hereinafter be made with reference to this position.

The products 5 are stored in a hopper 4 following the vertical axis Z-Z', in the operating position, having, such as represented, the shape of a funnel and comprising a discharge means 4*a* in the form of a partially-lower orifice, and a cover 4*b* in the upper portion. This hopper 4 is contained in an enclosure 8, advantageously an enclosure provided to maintain a setpoint temperature, as will be explained in further detail below. The orifice 4*a* opens onto the lower face 8*a* of the enclosure, which enables the products to flow from the hopper 4 and out of the enclosure 8.

A cylindrical support 2 is placed at a distance d under the lower face 8*a* of the enclosure. This cylinder is rotationally mounted about an axis A-A' orthogonal to the axis Z-Z' of the hopper. The support could have a shape other than cylindrical; it could for example be spherical. Depending on the intended use, the distance d is between 1 and 3 cm, although it is not limited thereto.

From the lower face 8*a* of the enclosure and at the periphery of the orifice 4*a*, in the direction of the cylinder 2, extends a set of flexible components (for example threads, filaments, hairs, thin strips, although not limited thereto) forming a brush 3. The components of the brush 3 form a soft wall defining a volume wherein the products 5 present in the hopper 4 can fall by gravity into a cavity of the support 2: this volume therefore brings the opening 4*a* of the hopper into communication with the cavity. The volume can be any kind of shape: cylindrical, conical, etc. This brush 3 is therefore different from other known brushes, in that it is substantially "hollow" and forms a flexible channel through which the products can flow from the orifice 4*a* of the hopper 4 towards a cavity 1*a*, 1*b*, without being dispersed.

Such as represented, the cylinder 2 comprises two cavities 1*a*, 1*b* at the surface thereof, the cavity 1*b* being concealed by the brush 3. The cavities 1*a*, 1 *b* can be any shape, but preferably a spherical shape; for a greater volume, they can extend along a generator of the cylinder 2. The number of cavities at the surface of the support could be different than two.

The brush 3 has two purposes:

- Thanks to the volume it defines, it guides the fragile products 5 from the orifice 4*a* towards a cavity 1*a*, 1 *b* when the cavity is located facing the orifice 4*a*; it thereby prevents the dispersion of the fragile products between the hopper 4 and the support 2,
- It reduces the shear stress applied to the fragile products when the cylinder 2 rotates, thereby reducing the risk of said fragile products being damaged.

The length of the components of the brush 3 is such that the free ends of these components are in permanent contact with the surface of the support 2 and brush said surface as it rotates. The components of the brush 3 are not necessarily all of the same length. The free ends of these components form a curve that reproduces the shape of the intersection of the volume defined by the brush 3 and the support 2 in order to guarantee a good seal between the brush 3 and the support 2, and on the other hand, to limit the friction stress on the fragile products. Thus, in the event where the brush 3 defines a volume with a cylindrical shape with a circular base:

- In the case where the support 2 is a cylinder, the free ends of the components of the brush 3 form a left curve which is that of the intersection of both cylinders, and consequently the components of the brush 3 are not all the same length.
- In the case where the support 2 is a sphere, the free ends of the components of the brush 3 form a curve which is that of the intersection of a cylinder and a sphere, i.e. a circle (insofar as the axis of the cylinder passes through the centre of the sphere), in which case the components of the brush 3 are all the same length.

In addition, the arrangement of these components is such that, when the opening 4*a* is located facing a cavity 1*a*, 1*b*, the free ends thereof surround the periphery of the cavity, so as to prevent the dispersion of fragile products between the brush and the support 2.

When the support 2 continues the rotation thereof, the products 5 which had fallen in a cavity 1*a*, 1 *b* are brushed by the brush 3 and can escape from the cavity. In FIG. 2, the support 2 has begun the rotation thereof and the fraction of products 5*a* that have fallen in the cavity can start escaping from it (arrow F).

FIG. 1 represents groups of such products 5*a*, collected in an ejection means 7, which, in this case, is shaped like a funnel. The funnel comprises an output duct 7*a* that guides the groups 5*a* of products towards the outside of the device 10. This ejection means 7 and the output duct 7*a* thereof are advantageous in the case where the device is loaded in a transport means, such as an aircraft, to ensure the products undergo a "soft" transition between the inside of the device and the outside. FIG. 1 also represents a group 5*b* of such products that have exited the device 10.

The device 10 thus enables to drop precisely-measured quantities of fragile products in the environment without damaging them. It is understood that it is easy to adjust the measured quantities by changing the shape and/or the number of cavities 1*a*, 1 *b*, as well as the rotational speed of the support 2. In addition, this rotational speed is not necessarily constant, it being able to progress step-by-step.

The fragile products to be dropped are for example seeds, biocides, bacterial spores (such as sporulation as toxic protein crystal for the insects of, for example, *Bacillus thuringiensis israelensis* (Bti) and *Bacillus sphaericus* (Bs)), but the device is advantageously used to drop, in a precisely calibrated manner, insects that have been sterilised by irradiation or genetically modified to fight certain diseases such as malaria and arboviruses or African trypanosomiasis transmitted by *glossina* (tsetse fly). The dropped insects start competing with "natural" insects, but do not produce offspring. They can also be parasitoids.

In this case, it is useful that the insects are maintained at a relatively low temperature, of between 8° C. and 10° C., and therefore lethargic, inside the hopper 4. In this case, the enclosure 8 forms a thermal barrier and the device 10 comprises a means to supply cold or, alternately, is suitable for receiving cold bodies such as freezer packs that change phase at a given temperature and/or dry ice.

The insects do not all have the same fragility, and the components of the brush 3 are advantageously adapted to the type of insect to drop. For example, *glossina* is a relatively resistant fly and the hair or the threads of the brush 3 can be relatively rigid. In contrast, mosquitoes are fragile and the "hairs" of the brush 3 will have to be a lot softer in order not to injure them. The components of the brush 3 can be chosen from among natural fibres (boar bristles, etc.) or artificial fibres. They can also be flexible thin strips. A person skilled in the art will know how to select the type of fibre or thin strips suitable for any insect.

FIGS. 3A and 3B illustrate another embodiment of the device. The entire upstream section of the device is identical to the example of FIGS. 1 and 2: hopper 4, enclosure 8, and brush 3. However, in this embodiment, the support is not moved rotationally but by a translational motion and it is made of a plate 20.

In the illustrated example, the plate 20 comprises two transversal cavities 10a, 10b. The plate 20 is moved in a back-and-forth motion so as to present facing the orifice 4a of the hopper 4, sometimes the first cavity 10a, and sometimes the second cavity 10b. When the cavity 10a is facing the orifice 4a (FIG. 3A), it is filled with fragile products and the second cavity 10b is emptied. The plate 20 then moves towards the left (arrow F1) to find itself in the position of FIG. 3B, wherein the cavity 10a is emptying and the cavity 10b is being filled. Then, the plate 20 returns to the position of FIG. 1 by moving towards the right (arrow F2).

For the cavity located facing the orifice 4a to fill without emptying at the same time, and to guide the products out of the cavity that is to be emptied, the plate slides between two fixed guides, an upper guide 11a and a lower guide 11b. The upper guide 11a comprises a transversal opening located facing the orifice 4a, so as to enable the filling of the cavity located facing the orifice 4a, and extends substantially on either side of this opening. On the contrary, the lower guide 11b comprises a full part located facing the orifice 4a.

In this manner:
- As illustrated in FIG. 3A, the first cavity 10a is filled with fragile products, which cannot escape as the cavity is closed in the lower part thereof by the lower guide 11b, while the second cavity 10b is being emptied, the products being prevented from escaping from the upper part of the cavity by the right wing of the guide 11b,
- FIG. 3B illustrates the mirror situation, wherein the second cavity 10b is being filled with fragile products, which cannot escape as the cavity is closed in the lower part thereof by the lower guide 11b, while the first cavity 10a is being emptied, the products being prevented from escaping from the upper part of the cavity by the left wing of the guide 11b.

To avoid injuring the fragile products during movements of the drawer of the support 20, the periphery of the openings 10a, 10b is advantageously equipped with small brushes 30.

In another version of this embodiment, the support 20 could be circular and rotationally-driven about an axis parallel to the Z-Z' axis of the hopper.

The invention claimed is:

1. A device for dropping fragile products comprising:
   a storage means of said products, comprising a discharge means of said products,
   a distribution means of the fragile products comprising at least one cavity provided at a surface of a support, the support being configured to take at least two positions, a first position wherein the at least one cavity is located facing and at a non-zero distance from said discharge means and is configured to be filled with fragile products, and a second position wherein said at least one cavity is spaced apart from said discharge means and is configured to be emptied,
   wherein said device comprises a flexible means of communication of the discharge means with the at least one cavity in order to fill the at least one cavity with fragile products, said flexible means of communication defining a volume connecting the discharge means and the support.

2. The device for dropping fragile products according to claim 1, wherein the flexible means of communication extends from a periphery of the discharge means.

3. The device for dropping fragile products according to claim 1, wherein the flexible means of communication comprises flexible components provided to ensure guiding of the products when said products fall in one of the at least one cavity located facing the discharge means.

4. The device for dropping fragile products according to claim 3, wherein a free end of the flexible components is in contact with a surface of the support, and with a periphery of one of the at least one cavity when this cavity is facing the discharge means.

5. The device for dropping fragile products according to claim 3, wherein the flexible components are threads, filaments, hairs or thin strips.

6. The device for dropping fragile products according to claim 1, wherein the support is a sphere rotationally mounted, or a cylinder rotationally mounted about an axis.

7. The device for dropping fragile products according to claim 1, wherein the at least one cavity is of a hemispherical shape.

8. The device for dropping fragile products according to claim 1, further comprising an ejection means configured to collect the products that have exited one of the at least one cavity and to guide said products towards an exterior of the device.

9. The device for dropping fragile products according to claim 1, further comprising an enclosure that forms a thermal barrier, said enclosure enclosing the storage means.

10. The device for dropping fragile products according to claim 1, further comprising a control means provided to adjust a speed of motion of the support.

11. A vehicle comprising a device according to claim 1.

12. A method for dropping insects using a device according to claim 1, comprising:
    filling the storage means with insects,
    activating the support so as to drop the insects.

13. The method for dropping insects according to claim 12, further comprising, before filling the storage means with insects, cooling the storage means so as to make or keep the insects lethargic.

14. The method for dropping insects according to claim 12, further comprising, before filling the storage means with insects, loading the device into a vehicle.

15. The method for dropping insects according to claim 14, wherein the vehicle is an aircraft so as to perform the insect drop in-flight.

16. The method for dropping insects according to claim 12, wherein the insects are sterilized by irradiation or genetically modified so that an offspring thereof is not viable.

* * * * *